(12) United States Patent
Ohira et al.

(10) Patent No.: US 6,347,284 B1
(45) Date of Patent: Feb. 12, 2002

(54) SYSTEM FOR PREDICTION OF ADHESION ENERGY AT INTERFACE BETWEEN DISSIMILAR MATERIALS AND METHOD THEREOF

(75) Inventors: Tatsuya Ohira; Yukihiko Inoue, both of Yokohama (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/126,739

(22) Filed: Jul. 31, 1998

(30) Foreign Application Priority Data

Aug. 1, 1997 (JP) .............................. 9-207580
Oct. 9, 1997 (JP) .............................. 9-276794

(51) Int. Cl.⁷ .............................. G01L 1/00; G01L 3/00; B32B 31/00
(52) U.S. Cl. .............................. 702/41; 702/30; 702/43; 702/182; 156/64; 156/378
(58) Field of Search .............................. 702/19, 22, 23, 702/26, 27, 30–33, 41–44, 81–84, 181–183; 156/64, 378

(56) References Cited

U.S. PATENT DOCUMENTS 4,008,567 A * 2/1977 Hirsch ...................... 60/39.282
5,438,402 A * 8/1995 Gupta ........................ 356/35.5
5,575,868 A * 11/1996 Mann ........................... 156/64

OTHER PUBLICATIONS

Baskes, Modified embedded potentials for cubic materials and impurities. Aug. 1, 1992. Physical Review B, vol. 46, No. 5, pp. 2727–2742.*

Yata et al., A Method of Adhesion Strength Test for Thick Film. Sep. 1993. IEEE Transactions on Components, Hybrids, and Manufacturing Technology, vol. 16, No. 6, pp. 584–591.*

Study of Machines, vol. 49, No. 4, pp. 28, 30–31, Aug. 1, 1992—Kenji Kakeko, "Strength and Adhesion Strength of Coatings" (English language translation provided).

Physical Review B, vol. 46, No. 5, pp. 2727–2742, Aug. 1, 1992—M. I. Baskes, "Modified embedded–atom potentials for cubic materials and impurities".

Physical Review Letters, vol. 50, No. 17, pp. 1285–1288, Apr. 25, 1983—Murray S. Daw and M. I. Baskes, "Semiempirical, Quantum Mechanical Calculation of Hydrogen Embrittlement in Metals".

* cited by examiner

Primary Examiner—Marc S. Hoff
Assistant Examiner—Manuel L. Barbee (57) ABSTRACT

A computer assisted system predicting adhesion energy at an interface between dissimilar materials, and an associated adhesiveness includes units for inputting given compositions and crystal structure of the dissimilar materials; like-atom and two unlike-atom interatomic interaction energy parameters on the dissimilar materials; and material interface atomic structure model information into a computer. The computer calculates a material interface total energy relative to a distance between surfaces of the dissimilar materials on the basis of the sum of the two like-atom and two unlike-atom interatomic interaction energies and evaluates the adhesion energy from the distribution of the calculated material interface total energy.

5 Claims, 4 Drawing Sheets

SYSTEM FOR PREDICTION OF ADHESION ENERGY AT INTERFACE BETWEEN DISSIMILAR MATERIALS AND METHOD THEREOF

BACKGROUND OF THE INVENTION

1. Field of the Invention

This invention relates to a system for a prediction of adhesion energy at an interface between dissimilar materials. The system predicts adhesion energy at the material interface (the energy necessary for separating two materials sufficiently remotely), or the presence or absence of adhesiveness, i.e., the parameters important for evaluation of the interfacial strength of various film materials as well as for the development of inhibitors of depositing substances.

2. Description of the Related Art

Some reports have been made on earlier technologies for experimentally measuring adhesion strength between various film-shaped dissimilar materials. Those technologies include one involving a scratch test (a testing method in which a diamond needle is pressed vertically against a coating film, the substrate is moved horizontally with a gradual increase in vertical load, to detect the occurrence of an acoustic wave or the like associated with the peeling or breakage of the film, and the load imposed at that time (critical load $W_c$) is measured to evaluate the adhesiveness; ("Study of Machines", Vol. 49, No. 4, pp. 30–31). However, the conventional techniques pose the major problem that even when the same test material and the same measuring instrument are used, the reproducibility and reliability of the results of measurement are not satisfactory.

No earlier technologies have existed for the theoretical prediction of adhesion strength at the interface between various film-shaped dissimilar materials. New technologies that can realize this prediction are in demand.

SUMMARY OF THE INVENTION

An object of the present invention is to provide a system for prediction by which adhesion energy corresponding to the strength of adhesion between dissimilar materials, or the presence or absence of adhesiveness can be theoretically evaluated, without the actual measurement of the adhesion strength, if the crystal structures and the compositions of the materials are known.

The system of the present invention for attaining the above-mentioned object is a system for predicting at least one of an adhesion energy at an interface between dissimilar materials and an adhesiveness, comprising:

a first read-in unit for reading given compositions and crystal structures of the dissimilar materials;

a second read-in unit for determining all of two like-atom and two unlike-atom interatomic interaction energy parameters on the dissimilar materials;

a third read-in unit for reading material interface atomic structure model information;

a computation unit for calculating a material interface total energy relative to a distance between surfaces of the dissimilar materials on the basis of the sum of the two like-atom and two unlike-atom interatomic interaction energies; and an evaluation unit for evaluating the adhesion energy from the distribution of the calculated material interface total energy.

The system for prediction of adhesion energy at the interface between dissimilar materials, in accordance with the present invention, makes it possible to calculate total potential energy relative to the distance between the surfaces of the two dissimilar materials by the use of an equation which expresses the interatomic interaction potential energies of diatomic systems related to the constituent atoms of the subject materials, and to predict the presence or absence of adhesiveness or adhesion strength (adhesion energy) from the distribution of the total energy.

DETAILED DESCRIPTION OF THE PREFERRED EMBODIMENTS

Preferred embodiments of the system for prediction of adhesion energy at the interface between dissimilar materials in accordance with the present invention will now be described in detail with reference to the accompanying drawings. However, it is to be understood that these embodiments are given only for illustrative purposes and do not restrict the invention.

Figure 1:
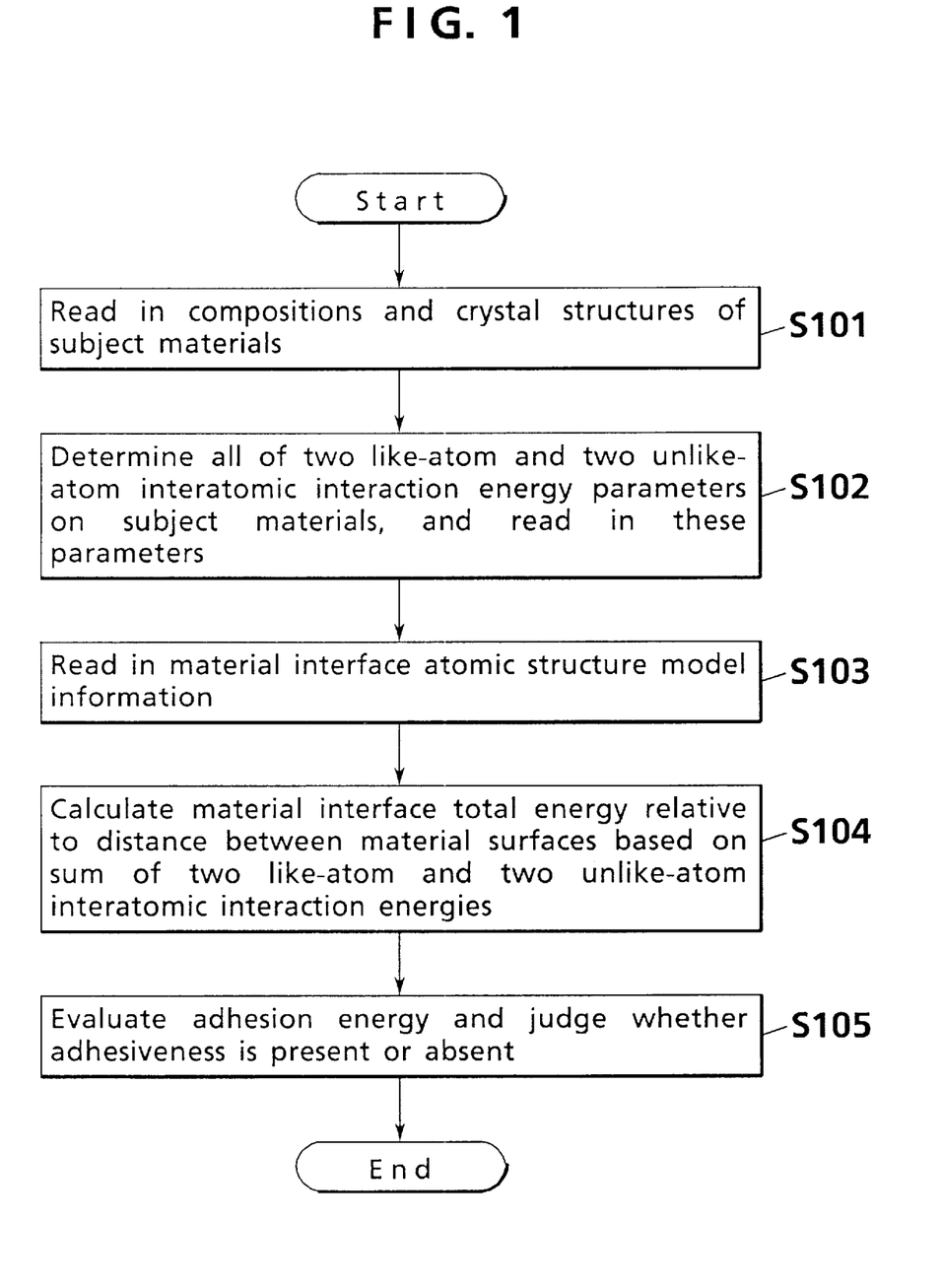
FIG. 1 is a view showing a flow of processings by the system for prediction of adhesion energy at the interface between dissimilar materials.
Figure 2:
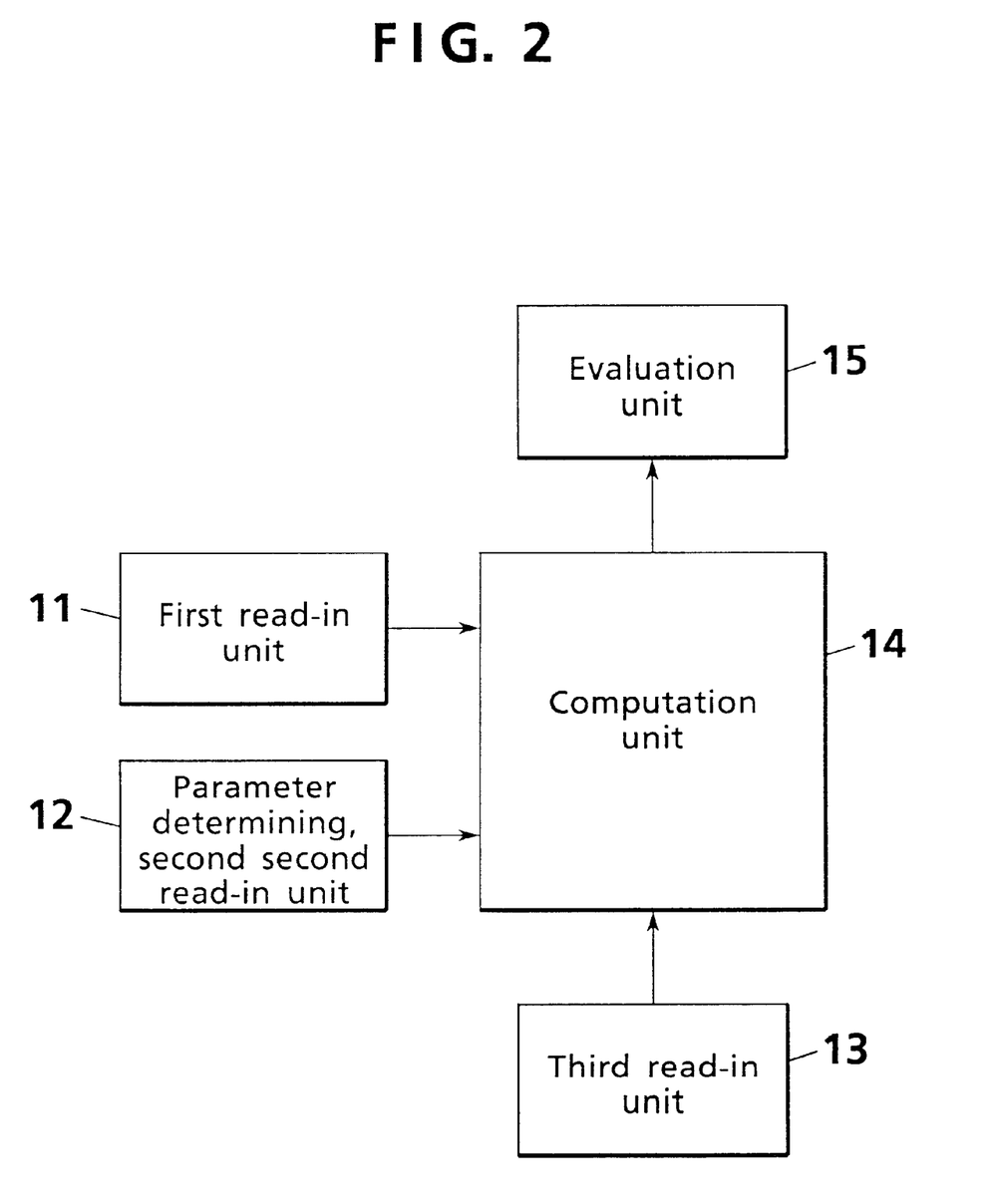
FIG. 2 is a block diagram of the system for prediction of adhesion energy at the interface between dissimilar materials.
Figure 3:
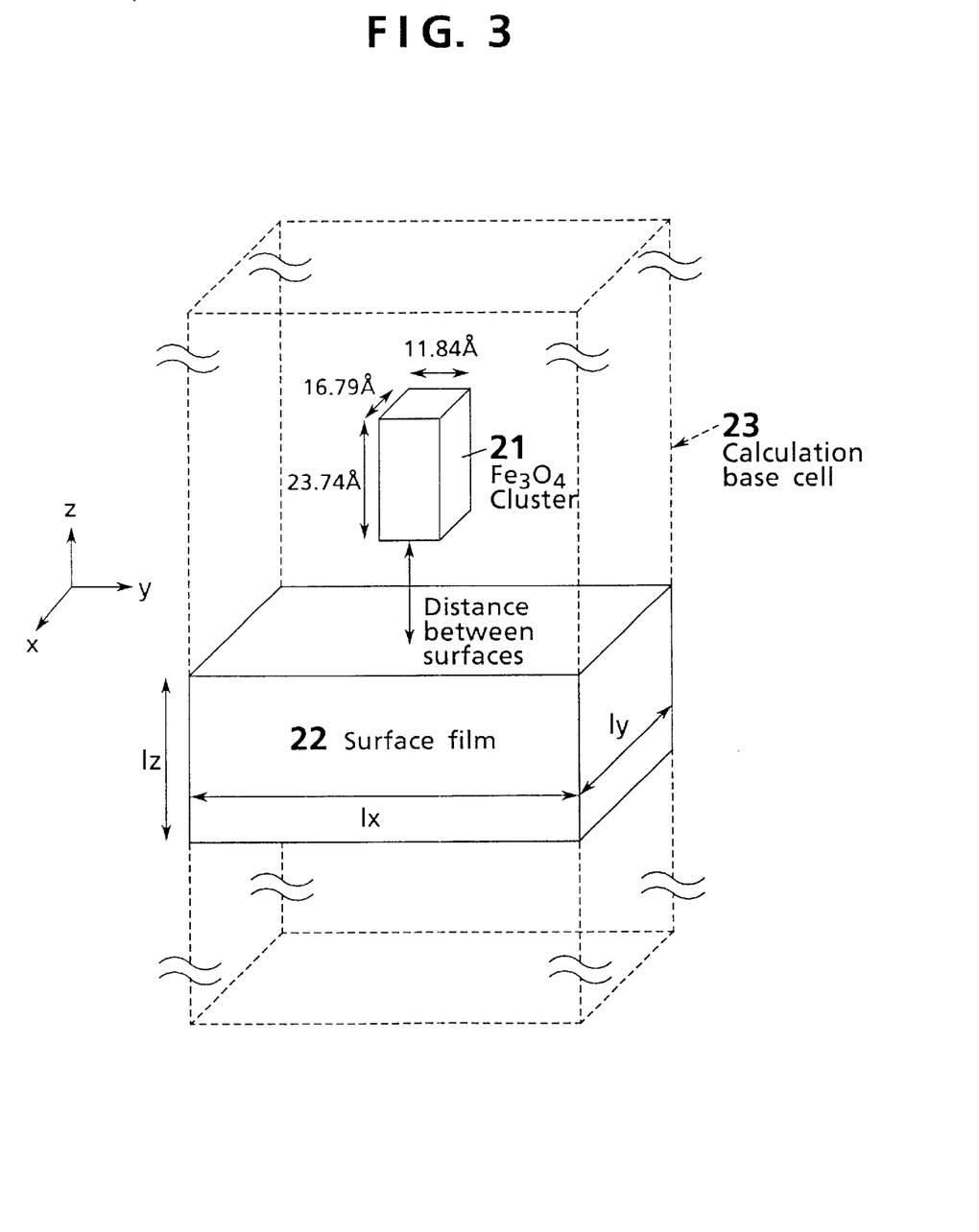
FIG. 3 is a view of a model for the interface between dissimilar materials, especially, an interface model for evaluation of adhesion energy between an oxide and an instrument surface film.

FIG. 1 is a view showing a flow of processings by the system for prediction of adhesion energy at the interface between dissimilar materials. FIG. 2 is a block diagram of the system for prediction of adhesion energy at an interface between dissimilar materials. FIG. 3 is a view of a model for the interface between dissimilar materials, especially, an interface model for evaluation of adhesion energy between an oxide and instrument surface films.

The two-atom interatomic interaction energy function, as a basis for the adhesion energy prediction system of the present invention, relies on the modified embedded-atom method (MEAM) made known by Physical Review B, Vol. 46, No. 5, 1992, pages 2727–2742. Hereinbelow, this function is called the MEAM potential function.

The MEAM potential function is based on the concept of the interatomic interaction energy function according to the embedded-atom method (EAM) which states that potential energies received by a certain atom is given by the sum of a half of the sum of the two-body force energies between the atom and neighbors, and the energy for embedding the atom into electron clouds given by all the neighbors. The EAM interatomic interaction energy function is called the EAM potential function.

The EAM potential function is known from Physical Review Letter, Vol. 57, No. 17, 1983, pages 1285–1288. However, this EAM potential function was applicable only to metals other than transition metals, because the electron cloud was an isotropically distributed electron cloud.

The MEAM potential function, on the other hand, can be applied to transition metals and metal oxides, because an anisotropically distributed electron cloud can be taken into consideration. The MEAM potential function also includes a model in which only neighboring atoms are considered for a close-packed structure, and remote atoms can also be considered in the case of a loose-packed structure such as a surface.

Currently, the MEAM potential function can basically deal with 44 atom species in the periodic table, including body-centered cubic structure type, face-centered cubic structure type, hexagonal closest packed structure, and diamond structure type crystals, and is widely applicable to metal surface oxide films.

The MEAM potential function is simplified into a form given by the following equation (1):

$$E_i = F_i(\rho_i/Z_i) + \frac{1}{2}\sum_{j \neq i} \phi_{ij}(R_{ij})$$

where $E_i$ is the potential energy of each atom, $F_i$ is the energy to embed an atom i into the background electron density $\rho_i$, $Z_i$ is the number of first-neighbors to the atom i, and $\phi_{ij}$ is a pair potential energy between atoms i and j separated by a distance $R_{ij}$.

In connection with the aforementioned 44 atom species, the function parameters in the first term of Eq. (1), and the parameters of the unlike-atom interatomic interaction energy function $\phi_{ij}$ in the second term of Eq. (1) are described in the aforementioned paper on the MEAM potential function (Physical Review B, Vol. 46, No.5, 1992, page 2731, Table III). These parameters are also used in the present invention. A description of these parameters is offered in Table 1.

The parameters of the unlike-atom interatomic interaction energy function $\phi_{ij}$ in the second term of Eq. (1) are determined by the following procedure using the experimental values of the subject materials, such as sublimation energy, lattice constant, and bulk modulus:

There are four parameters of the unlike-atom interatomic interaction energy function $\phi_{ij}$ for the MEAM: ① a parameter, delta, on sublimation energy, ② a nearest-neighbor distance parameter $r_e$, ③ an energy exponential function decay parameter α, and ④ a two-atom-derived reference crystal type.

As the reference crystal type ④, a crystal structure of a two-atom-derived material is selected from B1 (NaCl type) or L1$_2$ (Ni$_3$Si type), the crystal structure of which the experimental values of sublimation energy and lattice constant are maximally known.

The parameters ① and ② are closely correlated to the sublimation energy and lattice constant, and thus are determined from the sublimation energy and lattice constant of the reference crystal, if their experimental values are available. If the experimental values on the reference crystal are unavailable, those parameters are determined from the sublimation energies and lattice constants of the subject materials. The parameter ③ is also determined from the sublimation energy and lattice constant of the reference crystal, if their experimental values are available. If the experimental values on the reference crystal are unavailable, this parameter is determined from the bulk moduli of the subject materials, since it is highly correlated to bulk modulus.

The parameters ① to ③ are determined by repeating the following steps (1) to (4):

(1) The parameters ①, ② and ③ are provisionally set, and a bulk crystal structure in initial configurations is structurally relaxed in a calculation base cell (the locations of the atoms are moved little by little until the total energy

TABLE 1

Parameters for the MEAM: Values listed are the sublimation energy $E_i^0$(eV), the equilibrium nearest-neighbor distance $R_i^0$(Å), the exponential decay factor for the universal energy function $\alpha_i$, the scaling factor for the embedding energy $A_i$, the exponential decay factors for the atomic densities $\beta_i^{(1)}$, and the weighting factors for the atomic densities $t_i^{(1)}$.

| | $E_i^0$ | $R_i^0$ | $\alpha_i$ | $A_i$ | $\beta_i^{(0)}$ | $\beta_i^{(1)}$ | $\beta_i^{(2)}$ | $\beta_i^{(3)}$ | $t_i^{(0)}$ | $t_i^{(1)}$ | $t_i^{(2)}$ | $t_i^{(3)}$ |
|---|---|---|---|---|---|---|---|---|---|---|---|---|
| Cu | 3.540 | 2.56 | 5.11 | 1.07 | 3.63 | 2.2 | 6.0 | 2.2 | 1 | 3.14 | 2.49 | 2.95 |
| Ag | 2.850 | 2.88 | 5.89 | 1.06 | 4.46 | 2.2 | 6.0 | 2.2 | 1 | 5.54 | 2.45 | 1.29 |
| Au | 3.930 | 2.88 | 6.34 | 1.04 | 5.45 | 2.2 | 6.0 | 2.2 | 1 | 1.59 | 1.51 | 2.61 |
| Ni | 4.450 | 2.49 | 4.99 | 1.10 | 2.45 | 2.2 | 6.0 | 2.2 | 1 | 3.57 | 1.60 | 3.70 |
| Pd | 3.910 | 2.75 | 6.43 | 1.01 | 4.98 | 2.2 | 6.0 | 2.2 | 1 | 2.34 | 1.38 | 4.48 |
| Pt | 5.770 | 2.77 | 6.44 | 1.04 | 4.67 | 2.2 | 6.0 | 2.2 | 1 | 2.73 | −1.38 | 3.29 |
| Al | 3.580 | 2.86 | 4.61 | 1.07 | 2.21 | 2.2 | 6.0 | 2.2 | 1 | −1.78 | −2.21 | 8.01 |
| Pb | 2.040 | 3.50 | 6.06 | 1.01 | 5.31 | 2.2 | 6.0 | 2.2 | 1 | 2.74 | 3.06 | 1.20 |
| Rh | 5.750 | 2.69 | 6.00 | 1.05 | 1.13 | 1.0 | 2.0 | 1.0 | 1 | 2.99 | 4.61 | 4.80 |
| Ir | 6.930 | 2.72 | 6.52 | 1.05 | 1.13 | 1.0 | 2.0 | 1.0 | 1 | 1.50 | 8.10 | 4.80 |
| Li | 1.650 | 3.04 | 2.97 | 0.87 | 1.43 | 1.0 | 1.0 | 1.0 | 1 | 0.26 | 0.44 | −0.20 |
| Na | 1.130 | 3.72 | 3.64 | 0.90 | 2.31 | 1.0 | 1.0 | 1.0 | 1 | 3.55 | 0.69 | −0.20 |
| K | 0.941 | 4.63 | 3.90 | 0.92 | 2.69 | 1.0 | 1.0 | 1.0 | 1 | 5.10 | 0.69 | −0.20 |
| V | 5.300 | 2.63 | 4.83 | 1.00 | 4.11 | 1.0 | 1.0 | 1.0 | 1 | 4.20 | 4.10 | −1.00 |
| Nb | 7.470 | 2.86 | 4.79 | 1.00 | 4.37 | 1.0 | 1.0 | 1.0 | 1 | 3.76 | 3.83 | −1.00 |
| Ta | 8.089 | 2.86 | 4.90 | 0.99 | 3.71 | 1.0 | 1.0 | 1.0 | 1 | 4.69 | 3.35 | −1.50 |
| Cr | 4.100 | 2.50 | 5.12 | 0.94 | 3.22 | 1.0 | 1.0 | 1.0 | 1 | −0.21 | 12.26 | −1.90 |
| Mo | 6.810 | 2.73 | 5.85 | 0.99 | 4.48 | 1.0 | 1.0 | 1.0 | 1 | 3.48 | 9.49 | −2.90 |
| W | 8.660 | 2.74 | 5.63 | 0.98 | 3.98 | 1.0 | 1.0 | 1.0 | 1 | 3.16 | 8.25 | −2.70 |
| Fe | 4.290 | 2.48 | 5.07 | 0.89 | 2.94 | 1.0 | 1.0 | 1.0 | 1 | 3.94 | 4.12 | −1.50 |
| C | 7.370 | 1.54 | 4.31 | 1.80 | 5.50 | 4.3 | 3.1 | 6.0 | 1 | 5.57 | 1.94 | −0.77 |
| Si | 4.630 | 2.35 | 4.87 | 1.00 | 4.40 | 5.5 | 5.5 | 5.5 | 1 | 3.13 | 4.47 | −1.80 |
| Ge | 3.850 | 2.45 | 4.98 | 1.00 | 4.55 | 5.5 | 5.5 | 5.5 | 1 | 4.02 | 5.23 | −1.60 |
| H | 2.225 | 0.74 | 2.96 | 2.50 | 2.96 | 3.0 | 3.0 | | 1 | 0.20 | −0.10 | 0.00 |
| N | 4.880 | 1.10 | 5.96 | 1.50 | 4.00 | 4.0 | | | 1 | 0.05 | 0.00 | 0.00 |
| O | 2.558 | 1.21 | 6.49 | 1.50 | 6.49 | 6.5 | 6.5 | | 1 | 0.09 | 0.10 | 0.00 | of the system related to the sublimation energy becomes minimal). The length of the calculation base cell related to the lattice constant is variable during structural relaxation.

The calculation base cell refers to a rectangular parallelopipedal box where the atoms are initially configured. On this box, periodical boundary conditions are imposed in three directions, i.e., longitudinal, transverse and altitudinal directions. (See FIG. 3, which shows a base cell of an interfacial crystal structure, in particular, rather than a bulk crystal structure.)

(2) The sublimation energy and the lattice constant are calculated from the minimum energy and the cell length.

(3) Let the energy after analysis during structural relaxation (the cell length is variable) be $E_0$, the base cell volume be V, and the base cell length be $L_0$. The energy after analysis during structural relaxation (the cell length is fixed) at (i) l=1.001 $l_0$ is designated as $E_+$, while the energy after analysis during structural relaxation (the cell length is fixed) at (ii) l=0.999 $l_0$ is designated as $E_-$. The bulk modulus B is calculated from $B=E''/9V$ and $E''=(E_+ +E_- 2E_0)/0.001^2$.

(4) The initially set parameters are changed so that the calculated values will agree with the experimental values.

In this manner, the unlike-atom interatomic interaction energy parameters can be determined.

Using the above-described two like-atom and two unlike-atom interatomic interaction energy functions for the MEAM potential, the system for predicting the adhesion energy on the surfaces of the materials is constituted from the following five steps ①, ②, ③, ④ and ⑤ as shown in FIG. 1:

<Step ①>

A first read-in step for reading the compositions and crystal structures of the subject materials into a computation unit (S101).

<Step ②>

A parameter determining, second read-in step for determining all of two like-atom and two unlike-atom interatomic interaction energy (MEAM potential) parameters on the subject materials, and reading these parameters into the computation unit (S102).

<Step ③>

A third read-in step for reading in material interface atomic structure model information (S103)

<Step ④>

A computation step for calculating material interface total energy relative to the distance between the surfaces of the materials on the basis of the sum of the two like-atom and two unlike-atom interatomic interaction energies (S104).

<Step ⑤>

An evaluation step for evaluating adhesion energy from the distribution of the above total energy (S105).

The contents of each step are as follows:

At the first read-in step 101, the compositions (atom species and their proportions) and crystal structures (cubic crystal, hexagonal crystal, etc.) of the subject materials near the interface are entered into the computation unit.

Then, at the parameter determining, second read-in step S102, all combinations of two like-atoms and two unlike-atoms are extracted from the compositions of the subject materials entered into the computation unit at the first read-in step S101. Then, the two like-atom interatomic MEAM potential parameters described in Table 1 are used, while the two unlike-atom interatomic MEAM potential parameters are determined by the above-described method, whereafter these parameters are entered into the computation unit.

At the third read-in step S103, a model for an atomic structure at the interface of the materials, as illustrated in FIG. 3, is developed from information, such as the crystal structures and compositions entered at the first read-in step S101, as well as the directions of the material surfaces, and the planar horizontal relative positions of the atoms of the dissimilar materials facing each other. Then, the number of the atoms and the coordinates of the atomic configurations are entered into the computation unit. Based on the atomic coordinates entered, an interfacial atomic structure is formed in a calculation base cell for an adhesion energy prediction system.

In handling the interface structure of two materials in a calculation base cell, the atomic structures of both materials can be initially configured in the base cell, if their crystal structures and lattice constants are nearly identical. By imposing periodic boundary conditions in the interfacial horizontal direction, a model for a surface-surface system can be developed. If the surfaces of the two materials ate different in terms of the crystal structure or lattice constant, this is impossible.

Thus, one of the materials is handled as a cluster of a certain size so that the materials will be handled as a cluster-surface system model. In this case, however, it is evaluated how adhesion energy varies with the size of the cluster.

Then, at the computation step S104, the two materials are sufficiently separated, with the initial atomic configurations maintained, to cause structural relaxation and form surfaces. Then, with the use of the aforementioned interfacial atomic structure, material interface total energy versus the distance between the material surfaces is calculated on the basis of the sum of the two like-atom and two unlike-atom interatomic interaction energies.

Finally, at the evaluation step S105, adhesion energy is evaluated from the absolute value of the minimum of the total energy distribution relative to the surface-to-surface distance. Furthermore, the presence or absence of adhesiveness is judged from the presence or absence of an energy barrier in the energy distribution.

The system for prediction of adhesion energy at the interface between dissimilar materials of the present invention, which realizes the foregoing procedure, comprises, as shown in FIG. 2, a first read-in unit 11 for reading given compositions and crystal structures of the subject materials into a computation unit; a parameter determining, second read-in unit 12 for determining all of two like-atom and two unlike-atom interatomic interaction energy parameters on the subject materials, and reading these parameters into the computation unit; a third read-in unit 13 for reading in material interface atomic structure model information; the computation unit 14 for calculating material interface total energy relative to the distance between surfaces of the materials on the basis of the sum of the two like-atom and two unlike-atom interatomic interaction energies; and an evaluation unit 15 for evaluating adhesion energy from the distribution of the total energy.

EXAMPLE

An example of prediction of adhesion strength or the presence or absence of adhesiveness between iron oxide scale deposited on the surface of a piping instrument and various instrument surfaces in accordance with the present invention will be described by reference to the accompanying drawings. However, the invention is not restricted thereto.

At the first read-in step S101 of the process chart shown in FIG. 1, the compositions (atom species and their proportions) and crystal structures (cubic crystal, hexagonal crystal, etc.) of subject materials near an interface were entered into a computation unit.

In this Example, three types of surfaces, a SUS surface, a Cr-plated surface, an iron-containing Cr-plated surface, were each employed as the surface of an instrument.

The compositions and crystal structures of iron oxide scale (magnetite), a SUS surface oxide film, a Cr-plated surface oxide film, and an iron-containing Cr-plated surface oxide film were $Fe_3O_4$/cubic crystal (spinel), $NiFe_2O_4$/cubic crystal (spinel), $Cr_2O_3$/hexagonal crystal (corundum), and $FeCr_2O_4$/cubic crystal (spinel) All these pieces of information were entered into the computation unit.

To verify the validity of these parameters, the analyzed or predicted values of the sublimation energy, lattice constant, bulk modulus, shear elastic constant, and surface energy of $Fe_3O_4$, $NiFe_2O_4$, $Cr_2O_3$, and $FeCr_2O_4$ were compared with their experimental values or theoretical estimates. The results of comparisons are shown in Table 3.

The parameters were determined so that the underlined analyzed values in Table 3 would agree with the experimental values. The analyzed values other than the underlined ones were predicted values.

TABLE 3

| Physical property of material | Results of calculation (experimental value) | | | |
| --- | --- | --- | --- | --- |
| | $Fe_3O_4$ | $NiFe_2O_4$ | $Cr_2O_3$ | $FeCr_2O_4$ |
| Sublimation energy (eV/atom) | <u>4.91</u>(4.95)* | 4.38 | <u>5.52</u>(5.52)* | 5.15 |
| Lattice constant $a_0$ (Å) | <u>8.399</u>(8.396)* | <u>8.342</u>(8.340)* | <u>4.964</u>(4.961)* | <u>8.381</u>(8.377)* |
| Lattice constant $c_0$ (Å) | | | <u>13.606</u>(13.599)* | |
| Bulk modulus (GPa) | 156(161) | 120(146) | 267(234) | 40(140~170) |
| Shearing modulus r** (GPa) | 133(97) | 82(81)* | | 190(80~110) |
| Shearing modulus r¹** (GPa) | | | 110(113) | |
| (001) surface energy (J/m²) | 3.5(~3.9) | 3.3(~4.1) | 5.1(~5.0) | 7.0(~6.2) |

*The parameters have been determined so that the underlined calculated values will agree with the experimental values. The other calculated values are predicted values.
**r = $C_{44}$, r¹ ($C_{11}$–$C_{12}$)/2

Then, at the parameter determining, second read-in step S102, all combinations of two like-atoms and two unlike-atoms were extracted from the compositions of the subject materials entered into the computation unit at the first read-in step 101. Then, the two like-atom interatomic MEAM potential parameters described in Table 1 were used, while the two unlike-atom interatomic MEAM potential parameters were determined by the aforementioned method, whereafter these parameters were entered into the computation unit.

The subject material systems in this Example were found to be $Fe_3O_4$—$Fe_3O_4$, $Fe_3O_4$—$NiFe_2O_4$, $Fe_3O_4$—$Cr_2O_3$, and $Fe_3O_4$—$FeCr_2O_4$. Thus, the combinations of two like-atoms and two unlike-atoms were Fe—Fe, Ni—Ni, Cr—Cr, O—O, Fe—O, Cr—O, Fe—Cr, Fe—Ni and Ni—O.

The two unlike-atom interatomic MEAM potential parameters determined this time are shown in Table 2.

TABLE 2

| | Reference crystal structure | delta | $r_e$ | α |
| --- | --- | --- | --- | --- |
| Fe—O | B1 (NaCl type) | −1.3650 | 2.1475 | 4.0000 |
| Cr—O | B1 (NaCl type) | −2.1000 | 2.1600 | 4.5800 |
| Fe—Cr | B1 (NaCl type) | −3.8500 | 2.7000 | 4.5000 |
| Fe—Ni | L1₂ ($Ni_3Si$ type) | −0.0110 | 2.5031 | 5.2000 |
| Ni—O | B1 (NaCl type) | −1.2465 | 2.0842 | 4.1000 | delta (eV): Parameter concerned with sublimation energy
$r_e$ (Å): Nearest-neighbor distance
α: Energy exponential function decay parameter Comparisons show that the analyzed or predicted values of the bulk modulus, elastic constant, and surface energy of $Fe_3O_4$, $NiFe_2O_4$, and $Cr_2O_3$ nearly agreed with the experimental values.

For $FeCr_2O_4$, the analyzed value of the bulk modulus was slightly smaller than the estimated or experimental value, while the values of the elastic constant, and the surface energy important for the evaluation of adhesiveness nearly agreed with the estimated or experimental values, thus verifying the validity of the determined parameters.

The so determined two like-atom and two unlike-atom interatomic MEAM potential parameters were entered into the system for prediction of adhesion energy at the interface between dissimilar materials.

Further, an atomic structure model of a material interface as shown in FIG. 3 was prepared at the third read-in step S103, and the coordinates of its atomic configurations were entered into the computation unit.

The scale was imitated by a rectangular parallelopipedal $Fe_3O_4$ cluster (110 surface) of 360 atoms (14 atomic layers in the z direction). As the surface oxide film, the following 5 types, ① to ⑤, were each used:

① $Fe_3O_4$ (110 surface), 2,340 atoms, 12 atomic layers thick, $l_x$=35.62 Å, $l_y$=41.98 Å, $l_z$=17.81 Å

② $NiFe_2O_4$ (110 surface), 2,340 atoms, 12 atomic layers thick, $l_x$=35.62 Å, $l_y$=41.98 Å, $l_z$=17.81 Å

③ $FeCr_2O_4$ (110 surface), 2,340 atoms, 12 atomic layers thick, $l_x$=35.62 Å, $l_y$=41.98 Å, $l_z$=17.81 Å

④ $Cr_2O_3$ (110 surface), 2,880 atoms, 12 atomic layers thick, $l_x$=39.68 Å, $l_y$=40.80 Å, $l_z$=17.18 Å

⑤ $Cr_2O_3$ (100 surface), 3,600 atoms, 14 atomic layers thick, $l_x$=40.80 Å, $l_y$=42.96 Å, $l_z$=19.84 Å

In FIG. 3, the numeral 21 denotes a cluster ($Fe_3O_4$), the numeral 22 represents a surface film, and a dashed line for the numeral 23 represents a calculation base cell. The coordinates of the positions of the atoms in this calculation base cell 23 were entered into the computation unit.

Then, at the computation step S104, the two materials in the calculation base cell 23 were sufficiently separated, with the initial atomic configurations maintained, to cause structural relaxation and form surfaces. Then, the material interface total energy versus the distance between surfaces of the materials was calculated on the basis of the sum of the two like-atom and two unlike-atom interatomic interaction energies.

Figure 4A:
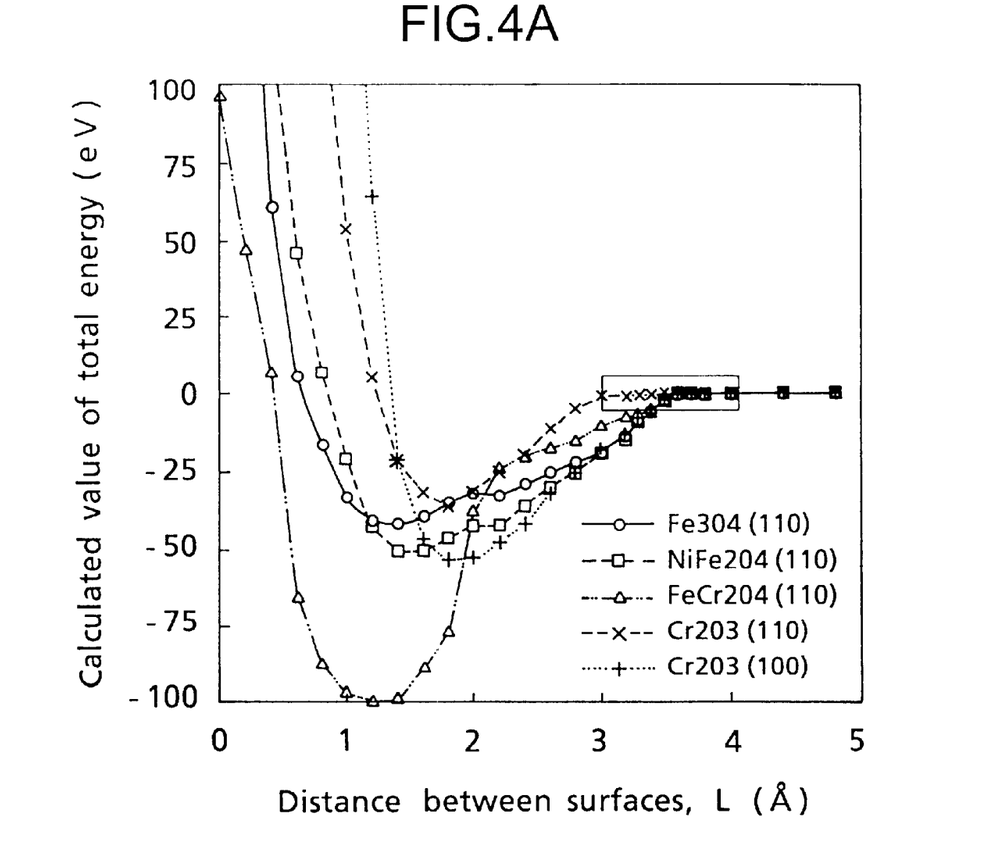
FIGS. 4A and 4B, hereinafter referred to as FIG. 4, are views showing the results of calculation of total energy versus the distances between an iron oxide and some instrument surface films.
Figure 4B:
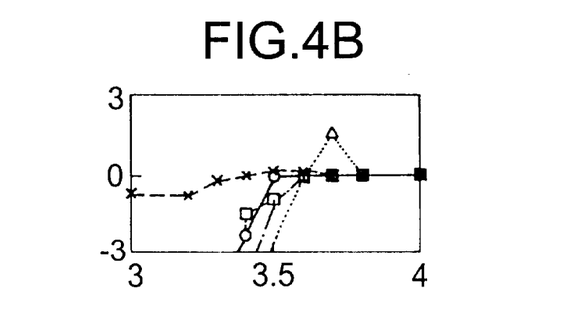

FIG. 4 shows the results of the static calculation of total potential energy obtained when the position of the scale, relative to each of the five types of oxide film surfaces used in the experiments, was varied by 0.2 Å at a time.

Finally, at the evaluation step S105, adhesion energy was evaluated from the absolute value of the minimum of the total energy distribution relative to the surface-to-surface distance. Furthermore, the presence or absence of adhesiveness was judged from the presence or absence of an energy barrier in the energy distribution.

Table 4 shows the results of calculation of the adhesion energy for the above 5 types of surfaces, as well as the presence or absence of energy barrier and the magnitude of the energy barrier.

TABLE 4

| Surface film | $Fe_3O_4$ | $NiFe_2O_4$ | $FeCr_2O_4$ | $Cr_2O_3$ (110) | $Cr_2O_3$ (100) |
|---|---|---|---|---|---|
| Adhesion energy ($J/m^2$) | 0.394 | 0.478 | 0.943 | 0.318 | 0.434 |
| Potential barrier (eV) | 0.0 | 0.0 | 0.0 | 0.18 | 1.56 |

The results in Table 4 showed that when the oxide film was the scale-deposited film ($Fe_3O_4$ (110 surface)), the SUS surface ($NiFe_2O_4$ (110 surface)), or the iron-containing Cr-plating ($FeCr_2O_4$ (110 surface)), there was no potential barrier, and the iron oxide scale ($Fe_3O_4$ (110 surface)) easily approached the surface film, becoming adhered and stable at an equilibrium position in each of the cases.

Furthermore, the adhesion energy for adhesion to the SUS surface was greater than that for the scale-deposited film surface. This finding demonstrated that scale easily adheres to the SUS surface, namely, that there is a high possibility for the formation of the scale film in a layered form, rather than in a columnar form.

When the oxide film was the Cr-plating ($Cr_2O_3$ (110 surface) or $Cr_2O_3$ (100 surface)), on the other hand, a potential barrier was found to exist in the total energy curve.

These barriers were about 0.2 eV and about 1.6 eV for $Cr_2O_3$ (110 surface) and $Cr_2O_3$ (100 surface), respectively. These values represent barriers minimally overcome by the kinetic energy (thermal level ~0.1 eV or less) of the scale itself appearing when the iron oxide scale approaches the surface film. With the iron-containing Cr-plating, as stated above, there is no potential barrier, so that the iron oxide scale is highly likely to adhere to it. These calculation results are in qualitative agreement with the experimental findings that adhesion to a Cr-plated surface does or does not take place depending on the conditions. These results demonstrate the usefulness of the system for prediction of adhesion energy at the interface between dissimilar materials in accordance with the present invention.

As described in detail by reference to the embodiments, the system for prediction of adhesion energy at an interface between dissimilar materials in accordance with the present invention is a system for prediction of adhesion energy at the interface between dissimilar film materials, which predicts adhesion energy at this interface, or the presence or absence of adhesiveness, the system comprising a first read-in unit for reading given compositions and crystal structures of the subject materials into a computation unit; a parameter determining, second read-in unit for determining all of two like-atom and two unlike-atom interatomic interaction energy parameters on the subject materials, and reading these parameters into the computation unit; a third read-in unit for reading material interface atomic structure model information; the computation unit for calculating a material interface total energy relative to a distance between surfaces of the materials on the basis of the sum of the two like-atom and two unlike-atom interatomic interaction energies; and an evaluation unit for evaluating adhesion energy from the distribution of the calculated material interface total energy.

Unlike the earlier technologies, therefore, even when the strength of adhesion between dissimilar materials has not been actually measured, adhesion energy corresponding to the adhesion strength, or the presence or absence of adhesiveness can be theoretically evaluated, if the crystal structures and the compositions of the materials are known.

What is claimed is:

1. A system for predicting at least one of an adhesion energy at an interface between dissimilar materials, and an adhesiveness, comprising:

a first read-in unit for reading given compositions and crystal structures of the dissimilar materials;

a second read-in unit for determining all of two like-atom and two unlike-atom interatomic interaction energy parameters on the dissimilar materials;

the like-atom interatomic interaction energy parameters for given like atoms being provided from predetermined values in a look-up table, the unlike atom interatomic interaction energy parameters being determined as a function of:

1) sublimation energy Δ, of each respective atom, 2) nearest-neighbor distance, re, for each respective atom, 3) an energy exponential decay parameter, α for each respective atom, and 4) a reference crystal type derived from two selected reference atoms;

approximating the unlike atom interatomic interaction energy for each respective atom by substituting known parameter of Δ, re and α for the selected reference atoms from known values thereof available in a look-up table;

a third read-in unit for reading material interface atomic structure model information;

a computation unit for calculating a material interface total energy relative to a distance between surfaces of the dissimilar materials on the basis of the sum of the two like-atom and two unlike-atom interatomic interaction energies; and an evaluation unit for evaluating the adhesion energy from the distribution of the calculated material interface total energy.

2. The system of claim 1, wherein said evaluation unit judges whether the adhesiveness is present.

3. The system of claim 1, wherein said dissimilar materials are dissimilar film materials.

4. A method for predicting at least one of an adhesion energy at an interface between dissimilar materials, and an adhesiveness, comprising:

reading given compositions and crystal structures of the dissimilar materials;

determining all of two like-atom and two unlike-atom interatomic interaction energy parameters on the dissimilar materials, the like-atom interatomic interaction energy parameters for given like atoms being provided from predetermined values in a look-up table, the unlike atom interatomic interaction energy parameters being determined as a function of:

1) sublimation energy $\Delta$, of each respective atom,
2) nearest-neighbor distance, re, for each respective atom,
3) an energy exponential decay parameter, $\alpha$ for each respective atom, and
4) a reference crystal type derived from two selected reference atoms;

approximating the unlike atom interatomic interaction energy for each respective atom by substituting known parameter of $\Delta$, re and $\alpha$ for the selected reference atoms from known values thereof available in a look-up table;

reading material interface atomic structure model information;

calculating a material interface total energy relative to a distance between surfaces of the dissimilar materials based on the sum of the two like-atom and two unlike-atom interatomic interaction energies; and evaluating the adhesion energy from the distribution of the calculated material interface total energy.

5. The method of claim 4, wherein said evaluating step includes the step of judging whether the adhesiveness is present.

\* \* \* \* \*